United States Patent [19]
Green et al.

[11] 3,991,849
[45] Nov. 16, 1975

[54] SOUND ABSORPTION WITH VARIABLE ACOUSTIC RESISTANCE MEANS

[75] Inventors: Gary Warner Green, Enfield; Ernest Feder, West Hartford, both of Conn.

[73] Assignee: United Technologies Corporation, Hartford, Conn.

[22] Filed: July 21, 1975

[21] Appl. No.: 597,630

Related U.S. Application Data

[63] Continuation-in-part of Ser. No. 481,004, June 19, 1974, abandoned.

[52] U.S. Cl. .............................. 181/33 H; 244/1 N; 415/119
[51] Int. Cl.² .......................................... E04B 1/99
[58] Field of Search ......... 181/33 H, 33 HB, 33 HC, 181/33 HA, 33 E, 336; 415/79, 119; 244/42 CE, 1 N

[56] References Cited
UNITED STATES PATENTS

| | | |
|---|---|---|
| 2,783,008 | 4/1957 | Bodine .............................. 181/33 H |
| 3,481,427 | 12/1969 | Dobbs et al. ...................... 181/33 H |
| 3,527,317 | 9/1970 | Motsinger ............................ 181/35 |
| 3,820,628 | 6/1974 | Hanson ......................... 181/33 HC |
| 3,831,710 | 8/1974 | Wirt................................ 181/33 H |
| 3,854,286 | 12/1974 | Klees .................................. 60/204 |

OTHER PUBLICATIONS

"Analytical & Experimental Studies for Predicting Noise Attenuation in Acoustically Treated Ducts for Turbofan Engines"; E. Feder & L. Dean; Boeing–Pratt & Whitney, 1969.

Primary Examiner—L. T. Hix
Assistant Examiner—Vit W. Miska
Attorney, Agent, or Firm—John D. Del Ponti

[57] ABSTRACT

A system for varying the acoustic resistance of an acoustical lining disposed in a duct of an air propulsor comprises a nonlinear sound suppression liner having a porous facing sheet overlying a plurality of cells, header means communicating with each of the cells and air pumping means for forcing a predetermined steady flow of air sequentially through the header means, the cells and the facing sheet to vary the acoustic resistance of the facing sheet to make it optimum for a selected sound level and airflow condition in the duct.

3 Claims, 7 Drawing Figures

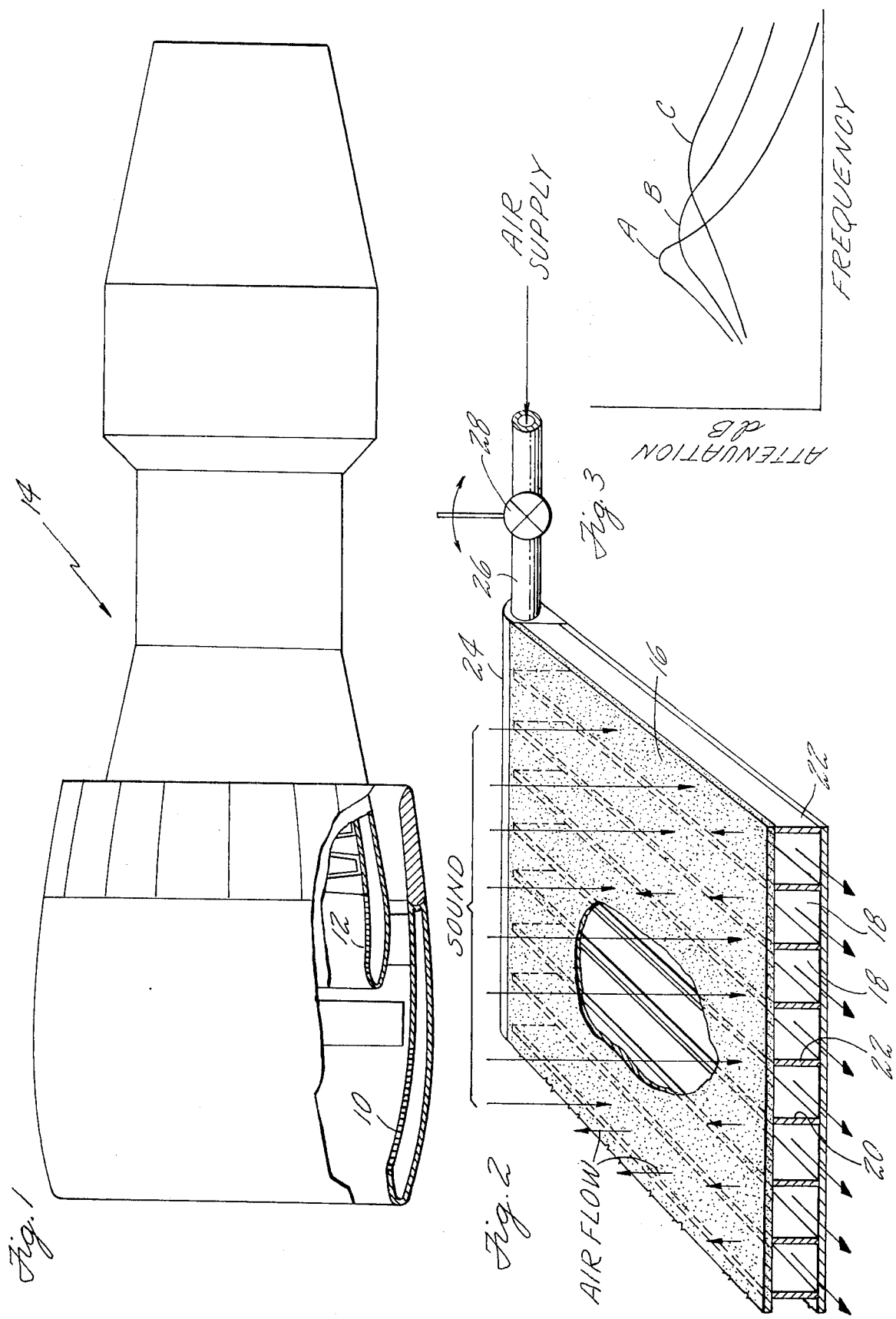

SOUND ABSORPTION WITH VARIABLE ACOUSTIC RESISTANCE MEANS

BACKGROUND OF THE INVENTION

This is a continuation-in-part application of Ser. No. 481,004 filed June 19, 1974 by the same inventors, now abandoned.

This invention relates to sound absorption systems and more particularly to a system for varying the acoustic resistance of an acoustical lining disposed in an air propulsor duct by providing means for selectively imposing a steady flow of fluid, such as air, through the lining.

A typical acoustical panel construction designed for aircraft use is described in U.S. Pat. No. 3,481,427 granted to R. A. Dobbs and R. N. Holmes where a porous sheet overlies a plurality of cavities that are deadended by an impervious backing sheet. Accordingly, transmission losses occur by passage of sound waves propagating over the porous surface into still air cavities, resulting in a sound level drop across the porous surface face.

One of the problems extant in optimizing duct lining material for air propulsor ducts centers on the fact that lining material environment during propulsor operation changes dramatically in sound level and grazing flow conditions. These environmental conditions in aircraft engine and APU inlet and exhaust ducts, for example, change significantly for different air flight modes, e.g., takeoff, cutback and approach, and APU operating power levels.

SUMMARY OF THE INVENTION

It is an object of this invention to maximize the attenuation of sound by varying the acoustic resistivity of nonlinear duct acoustical linings to optimize lining resistance throughout the range of changing conditions encountered thereby.

The present invention contemplates a system for adjusting the noise absorption quality of an acoustical lining by changing its acoustic properties so that its resistance will be optimum for the sound level and grazing flow conditions encountered by providing means for imposing a selected steady flow of air through the material.

In accordance with the present invention, a system for varying the acoustic resistance of an acoustical lining disposed in an air propulsor duct comprises a nonlinear sound suppression liner having a porous facing sheet and a substantially close-ended, side and bottom enclosure member defining a cavity and having an open top surface, the facing sheet extending over said top surface and a plurality of sidewalls extending between the facing sheet and the enclosure member in the cavity to divide the cavity into a plurality of cells, header means communicating with each of the cells, and air pumping means for forcing a predetermined steady flow of air sequentially through the header means, the cells and the facing sheet to vary the acoustic resistance of the facing sheet to make it linear for a selected sound level and grazing airflow condition in the duct. The duct lining may be constructed from a porous sheet overlying either channel or cellular sound absorption cavities dead-ended by an impervious hard back wall with means provided for conducting air through apertures formed in the hard back wall and/or adjacent channels and/or slots in the cell walls.

Some of the advantages of the present invention are:
1. Changes in liner acoustic resistance because of contamination of the duct lining due to dirt, oil, etc., may be compensated for by reducing the amount of airflow.
2. For applications for which the optimum acoustic properties are not too well known, they may be empirically determined after installation by varying the throughflow until a maximum attenuation is achieved.
3. If the major variations exist between units of the same design, they may be individually optimized using different through airflow settings.

BRIEF DESCRIPTION OF THE DRAWINGS

An understanding of the invention will become more apparent to those skilled in the art by reference to the following detailed description when viewed in light of the accompanying drawings, wherein:

FIG. 1 is an elevation view partly in section showing the lining in the duct of the inlet of a ducted fan and compressor section of a power plant;

FIG. 2 is an exploded perspective view partly in schematic illustrating a preferred acoustical panel configuration;

FIG. 3 is a graph plotting attenuation in decibels (dB) vs. frequency illustrating the effect of this invention;

DESCRIPTION OF THE PREFERRED EMBODIMENT

Figure 4:
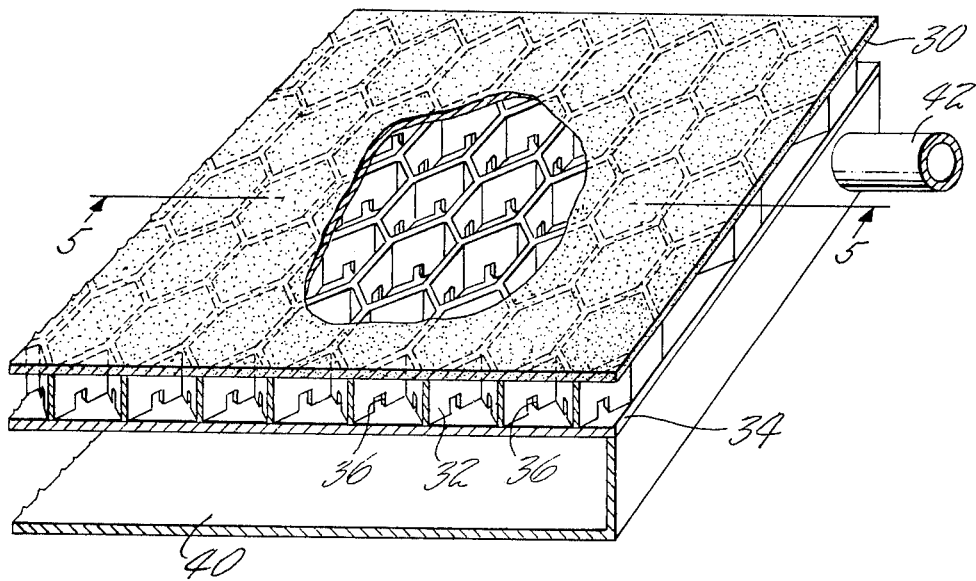
FIG. 4 is an exploded perspective view illustrating another preferred acoustical panel configuration.

As noted from FIG. 1 the linings 10 and 12 are in the inlet of the fan and compressor section of a propulsor generally illustrated by numeral 14 and are merely exemplary of locations for applying the lining material. As will be appreciated, the particular location of the lining is not important to this invention as the invention has contemplated use in any location where environmental conditions change, be it at the inlet or exhaust of an engine, ducted fan or auxiliary power unit.

The invention can best be understood by referring to FIG. 2 wherein the lining 10 and 12 is shown as comprising a nonlinear porous sheet 16 overlying open-ended channel cells 18 defined by adjacent, axially extending spaced walls 20 radiating from the nonporous hard back wall 22. As will be appreciated by those skilled in the art, porous sheets include metallic and nonmetallic plates with various kinds of perforations as well as fine meshes of woven metallic and nonmetallic fibers. One end of the channels 18 may be blocked off by an end plate or may be abutted against the wall of the structure to which it's mounted. A manifold or header 24 is mounted on the other end and serves to distribute air to all of the channels. An air feed line 26 feeds air to header 24 and valve 28 regulates the flow thereto. Obviously valve 28 may be manually adjusted and/or may automatically respond to any signal indicative of aircraft flight conditions as, for example, power lever position, airflow, etc. Suffice it to say that the purpose of the valve 28 is to regulate the airflow through the liner so as to achieve the desired sound attenuation characteristics.

It should be noted that the primary concept advanced herein centers on bringing the lining material, by means of steady airflow therethough, to various conditions of optimized resistance. Lining material is linear when the air velocity through the material is directly proportional to the pressure drop thereacross. Lining material is nonlinear when the aforesaid relationship between air velocity and pressure drop across the facing sheet is some function, e.g., a square or other function other than directly proportional.

Figure 7:
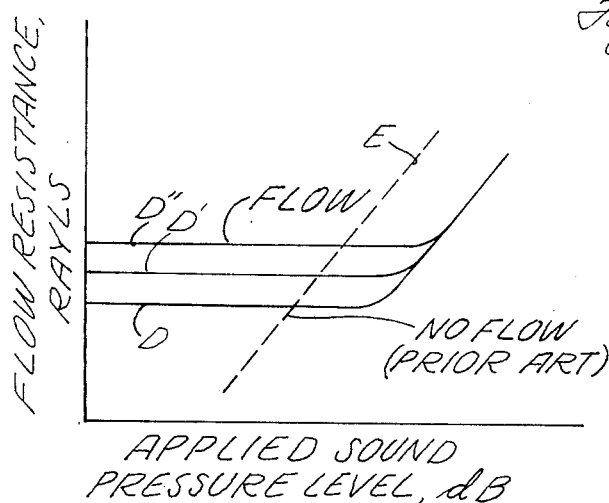
FIG. 7 is a graph showing the linearity of facing materials with and without flow plotted on log-log scale.

In essence, the quantity of air from the air supply flowing through the channels 18 and passing through the porous sheet 16 serves to tune the lining for a given condition, i.e., to optimize its resistance for maximum effective sound absorption. It has been found that a change in the flow and sound level in the duct (otherwise referred to as grazing flow) will vary the attenuation spectrum as is shown in FIG. 3. Curves A, B and C illustrate the attenuation spectrum for three different duct flow conditions in an exhaust duct - i.e., Curve A represents takeoff conditions which include high velocity grazing airflow, B, cutback conditions which include medium velocity grazing airflow, and C, approach conditions at approach which include low velocity grazing airflow. For each condition, there is an optimum resistance which will produce maximum noise reduction. The resistance of the lining may be made to behave as shown in Curve D, D' and D'' in FIG. 7 wherein the thru-flow of air from the air supply is adjusted to set the optimum flow resistance over the range illustrated for each condition encountered. Thus, the attenuation spectrum of Curve A, FIG. 3, will have a flow resistance illustrated by Curve D, Curve B by D' and Curve C by D''. Curve E is exemplary of a prior art liner not having thru-flow and having a different porosity, and shows that this characteristic is nonlinear. Thus, for duct lining environmental conditions which require increasing the acoustic resistance, a relatively large amount of air may be forced through the facing sheets. For duct environmental conditions requiring a smaller acoustic resistance, etc., less air is forced through. By controlling the amount of airflow from the air supply, the duct lining material may be optimized for any environmental conditions, the airflow being a steady amount for the selected acoustic resistance and the resistance being changeable by varying the liner airflow during flight. Although it is preferred that the airflow be provided in a direction toward the duct by supplying it through the cell to the porous face sheet, the direction is not critical and may be provided in a path from the duct by sucking air through the cell from the porous sheet.

Figure 5:
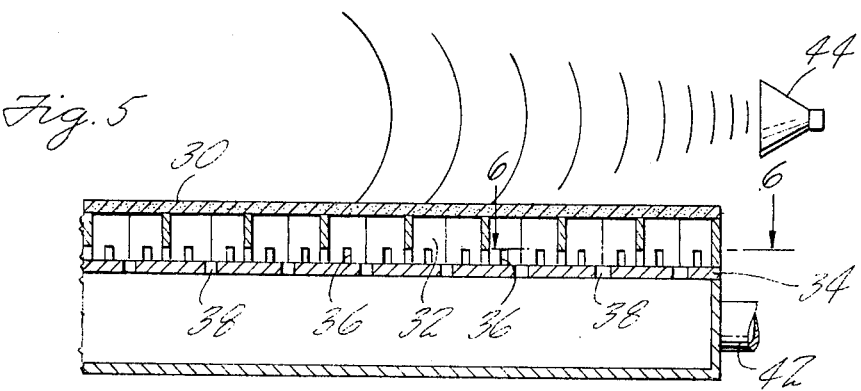
FIG. 5 is a section taken along line 5—5 of FIG. 4.
Figure 6:
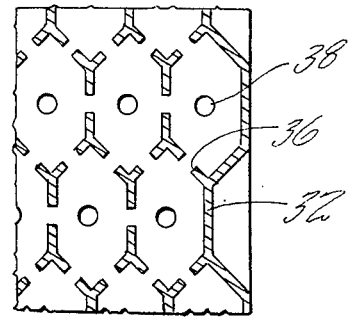
FIG. 6 is a section taken along line 6—6 of FIG. 5.

FIGS. 4, 5 and 6 illustrate another acoustical panel construction having a plurality of honeycomb acoustical or resonating cells. The porous sheet 30 overlies the honeycomb core 32 and a hard wall 34 is mounted on the back face. The honeycomb core consists of a network of sidewalls 35 as is known in the art. Typically, the sidewall network forms a plurality of identically shaped cells - in this case the cells are of hexagonal configuration. Apertures 38 are formed in wall 34 located so as to communicate with a selected number of the cells. A plurality of slots 36 are preferably formed on each of the sidewalls or back face of honeycomb core 32 so that each cell has an inlet in the case of air flowing into the cells from the wall 34 or an outlet if flow is sucked out of the cell through the back wall 34. Header 40 is mounted on the face of wall 34 and like header 24 serves to distribute air to each of the cells through apertures 38 so that the air flows through the cells, and then the porous sheet. If a vacuum or suction pump is utilized the flow will be sucked through the porous sheet 30, through the cells and out of header 40.

As shown in FIG. 5, acoustical resistivity may also be controlled by mounting a sound generator such as a horn driver 44 directly in the duct or in the duct wall.

The operation of the present invention may best be illustrated by the following example. For a duct environment wherein (1) at approach the noise sound level is 145 dB and the grazing airflow is 300 ft/sec and (2) at takeoff the noise sound level is 155 dB and the grazing airflow is 500 ft/sec, it was determined that optimum flow resistance, in order to attain maximum or optimum attenuation, is provided by a lining material having a flow resistance of 40 rayls during approach and by a liner providing a flow resistance of 48 rayls during takeoff. Therefore, for approach, there exists an optimum resistance which is different than that for takeoff. A nonlinear liner comprising a hard wall backing, a layer of 0.75 inch deep, 0.75 inch honeycomb cells and either a perforated plate facing having 12 percent open area during approach or a perforated plate facing having 18 percent open area during takeoff, will provide the aforesaid optimum flow resistances. By following the teachings of the present invention, it will be appreciated that a single liner may be provided to obtain a plurality of attenuation maxima. For example, the liner having 18 percent open area may be utilized with no additional flow supplied by the air supply during takeoff so that the optimum flow resistance of 48 rayls and hence the maximum attenuation during that condition will obtain. During approach however, the airflow from the air supply is effected in an amount to render the same 18 percent open area liner to have a flow resistance of 40 rayls. Without the throughflow, the resistance under these new conditions would be only 27 rayls. In the present case, this is accomplished by a throughflow air velocity from the air supply, during approach, of 37.7 ft/sec.

It should be understood that the invention is not limited to the particular embodiments shown and described herein, but that various changes and modifications may be made without departing from the spirit or scope of this novel concept as defined by the following claims.

We claim:
1. A method for varying the acoustic resistance of a nonlinear acoustical lining having a porous facing sheet and a substantially close-ended, side and bottom enclosure member defining a cavity having a plurality of cells, said lining being disposed in a duct of an air propulsor subject to changing sound level and grazing airflow conditions comprising:
   connecting said liner to air passage means for communicating said cells therewith and forcing air through said cells; and
   forcing selected different amounts of air through said cells for different sound level and grazing airflow conditions in the duct to change the acoustic resistance of said liner to an acoustic resistance which is optimum therefor.

2. The method of claim 1 wherein each said selected amount of air is forced sequentially through said air passage means, said cells and said facing sheet.

3. The method of claim 1 wherein each said selected amount of air is forced sequentially through said facing sheet, said cells and said air passage means.

* * * * *

UNITED STATES PATENT OFFICE
CERTIFICATE OF CORRECTION

PATENT NO. : 3,991,849
DATED : November 16, 1976
INVENTOR(S) : Gary Warner Green and Ernest Feder It is certified that error appears in the above-identified patent and that said Letters Patent are hereby corrected as shown below:

On the first page of the Patent, in the upper right-hand corner, the date "Nov. 16, 1975" should read -- Nov. 16, 1976 --

Signed and Sealed this

Twenty-second Day of March 1977

[SEAL]

Attest:

RUTH C. MASON
Attesting Officer

C. MARSHALL DANN
Commissioner of Patents and Trademarks